Figure 1:
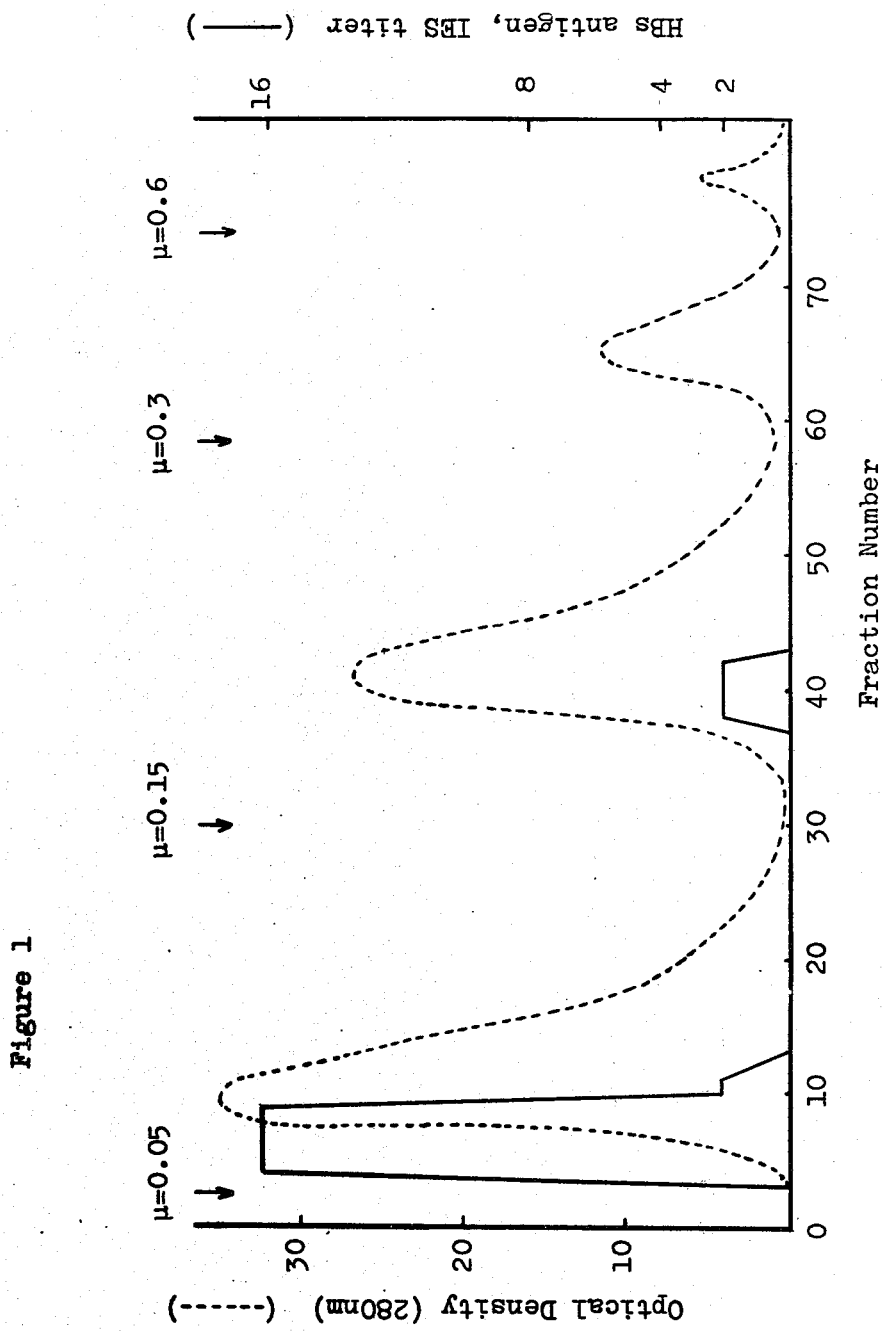

United States Patent [19]

Mizuno et al.

[11] 4,162,192

[45] Jul. 24, 1979

[54] METHOD FOR PURIFICATION OF HBS ANTIGEN

[75] Inventors: Kyosuke Mizuno; Atsushi Miyanohara; Yoshimitsu Ishihara; Nobuya Ohtomo, all of Kumamoto, Japan

[73] Assignee: Juridical Foundation, Kumamoto, Japan

[21] Appl. No.: 946,733

[22] Filed: Sep. 28, 1978

[51] Int. Cl.$^2$ .............................................. A61K 39/12
[52] U.S. Cl. ....................................... 435/239; 424/89
[58] Field of Search ............................ 195/1.5; 424/89

[56] References Cited
U.S. PATENT DOCUMENTS

| 3,976,767 | 8/1976 | Neurath | 195/1.5 X |
| 4,113,712 | 9/1978 | Funakoshi | 424/89 X |

*Primary Examiner*—Shep K. Rose
*Attorney, Agent, or Firm*—Stevens, Davis, Miller & Mosher

[57] ABSTRACT

An improved method for purification of HBs antigen comprising passing a partially purified HBs antigen prepared from blood plasma or serum through a column filled with an anion exchanger which may be equilibrated with a buffer solution having a specific ionic strength and pH level, and further passing the resulting effluent through a column filled with a cation exchanger which may be equilibrated with a buffer solution having a specific ionic strength and pH level. The HBs antigen obtained by the present invention is highly purified and is useful for preparing vaccine for preventing Viral Hepatitis Type B.

4 Claims, 2 Drawing Figures

METHOD FOR PURIFICATION OF HBS ANTIGEN

The present invention relates to an improved method for purification of a surface antigen of hepatitis type B virus which is usually called as Hepatitis B surface antigen and abbreviated as "HBs antigen". More particularly, it relates to a method for purification of HBs antigen by an ion exchange chromatography using a combination of an anion exchanger and a cation exchanger.

So-called serum hepatitis or posttransfusion hepatitis is a disease induced by infection with a virus having a size of 42 nm and containing a DNA type nucleic acid, which is called as Hepatitis Type B virus (hereinafter, referred to as "HB virus"), and this hepatitis is designated as "Viral Hepatitis Type B" by World Health Organization (WHO) in 1973.

The viral hepatitis type B has not yet been sufficiently studied, but attention has been paid to this disease because it tends to become a chronic state and it has a close relation with a chronic hepatitis, liver cirrhosis and hepatoma, and hence, it has been desired to exterminate this disease. For this purpose, it is recommended to use a vaccine prepared from surface antigen of the HB virus.

Antigens of HB virus include HBs antigen which is a surface antigen of HB virus; hepatitis type B core antigen which is a core antigen of the virus containing a nucleic acid and is usually abbreviated as "HBc antigen"; and an antigen which is still unclear but has a close relation with infectivity of HB virus and is usually abbreviated as "HBe antigen".

Blood of patients and carriers infected with HB virus contains a large amount of spherical particles and tubular structures of HBs antigen (size: 22 nm), which has no nucleic acid and may be a surface component of the virus as well as particles of HB virus (size: 42 nm, which is called as "Dane particle"), and hence, an antibody against the HBs antigen may play a role for neutralizing the virus infectivity.

Thus, HBs antigen is useful as a material of the vaccine for preventing viral hepatitis type B. However, since there has never completely successed in tissue culture of HB virus, HBs antigen must be prepared from blood of patients and carriers infected with HB virus, and hence, it is necessary to remove all components in such blood plasma other than HBs antigen such as plasma proteins, HBe antigen as well as HB virus.

Purification of HBs antigen has hitherto been done by various methods, such as ultracentrifugation, gel filtration, affinity chromatography, or a combination thereof. For instance, Gerin et al disclose a method for purification of HBs antigen by repeating twice an isopycnic centrifugation using cesium chloride by a zonal rotor, subjecting to a cushion centrifugation with sucrose and further subjecting to an isopycnic centrifugation [cf. Gerin et al, J. Virol. Vol. 7, 569 (1971) and J. Immunol. Vol. 115 (1), 100 (1975)]. Blumberg et al disclose a purification of HBs antigen by a combination of centrifugation, treatment with an enzyme, column gel filtration, and ultracentrifugation under density gradient with sucrose and cesium chloride (cf. Japanese Patent Publication No. 19603/1975). Besides, Houwen et al disclose a purification of HBs antigen by affinity chromatography which comprises conjugating an anti-HBs antibody to Sepharose 4B gel, treating a plasma, which is positive of HBs antigen by the resultant gel, and thereby eluting the HBs antigen adsorbed onto the gel. An article entitled "Isolation of Hepatitis B Surface Antigen (HB,Ag)" by Affinity Chromatography of Antibody-Coated Immunoadsorbents) by Houwen et al is published in the *Journal of Immunological Methods* 8 (1975), pages 185 to 194 printed in the Netherlands by North-Holland Publishing Company of Amsterdam. The eluate fraction of this method still contains blood serum components (e.g. prealbumin, albumin, transferrin, $\beta$-lipoprotein, $\alpha_2$-macroglobulin, $\gamma$-globulin), and hence, the fraction passed through Sepharose 4B gel column which is bonded with antibodies to normal human serum in order to remove these blood serum components.

These methods have some advantages but have also many drawbacks. For instance, the purification by ultracentrifugation requires to repeat several times the density gradient centrifugation using cesium chloride and sucrose and hence requires a large amount of cesium chloride and sucrose. Besides, the ultracentrifuging machine should be provided with various rotors in accordance with the degree of purification and the steps therefor. The gel filtration method is inferior in the capacity and is not suitable for the purification in a large scale. Moreover, this gel filtration method is also inferior in the degree of purification, and when the HBs antigen is prepared from blood plasma, there can not be obtained HBs antigen of high purity. The affinity chromatography method requires anti-HBs antibody, and hence, when it is carried out in a large scale, an enormous amount of anti-HBs antibody (human origin or an immunized animal origin) must be prepared all the time.

The present inventors have intensively studied on improvement of purification of HBs antigen and have found that the desired HBs antigen having a high purity can comparatively simply be obtained by an ion exchange method.

An object of the present invention is to provide an improved method for purification of HBs antigen. Another object of the invention is to provide a method for preparing a highly pure HBs antigen from blood plasma or serum. These and other objects of the invention will be apparent from the following disclosure.

According to the present invention, the desired HBs antigen is obtained by subjecting a partially purified HBs antigen prepared from blood serum or plasma to an ion exchange chromatography using an anion exchanger and a cation exchanger. That is, a partially purified HBs antigen obtained from blood plasma or serum of patients and carriers infected with HB virus by a conventional method is passed through an anion exchanger, whereby most of blood plasma components other than HBs antigen and certain plasma proteins comprising mainly $\gamma$-globulin are adsorbed, and then the effluent thus passed through the anion exchanger, which contains HBs antigen and certain plasma proteins, is further passed through a cation exchanger, whereby the plasma proteins comprising mainly $\gamma$-globulin are adsorbed and only the desired HBs antigen is contained in the effluent.

The present invention has been accomplished after extensively studying on the behavior of the HBs antigen onto anion and cation exchangers under various conditions. The purification of HBs antigen by the present invention is carried out by passing an HBs antigen-containing solution through an anion exchanger and a cation exchanger whereby impurities are adsorbed onto the exchangers.

There have been reported various methods for purification of virus using ion exchangers, for example, purification of *E. coli phage* [Creaser and Taussig, Virol, Vol. 4, 200 (1957)]; purification of tobacco mosaic virus [Cochran et al, Nature, Vol. 180, 1281 (1957)]; purification of polio virus [Hoyer et al, Science, Vol. 127, 859 (1958)]; and purification of vaccinia virus [McCrea and O'Loughlin, Virol, Vol. 8, 127 (1959)]. However, it has never been known to purify antigens of virus such as HBs antigen originated to blood plasma or serum without adsorbing onto ion exchanger.

The ion exchanger used in the present invention is to be repeatedly usable in column without specific activation and to have a large binding capacity and is preferably an autoclavable gel having excellent stabilities under various conditions, e.g. at various pH levels, ionic strengths, etc.

Suitable examples of the anion exchanger are agarose gel introduced with an anionic substituent (e.g. DEAE-Sepharose CL-6B), dextran gel introduced with an anionic substituent (e.g. DEAE-Sephadex, QAE-Sephadex), cellulose introduced with an anionic substituent (e.g. DEAE-cellulose, TEAE-cellulose), or the like. The anionic substituent includes diethyl-aminoethyl (DEAE), triethylaminoethyl (TEAE) and diethyl-(2-hydroxypropyl)aminoethyl (QAE).

Suitable examples of the cation exchanger are agarose gel introduced with a cationic substituent (e.g. CM-Sepharose CL-6B), dextran gel introduced with a cationic substituent (e.g. CM-Sephadex, SP-Sephadex), cellulose introduced with a cationic substituent (e.g. CM-cellulose), or the like. The cationic substituent includes carboxymethyl (CM), sulfopropyl (SP) and sulfoethyl (SE).

The partially purified HBs antigen used in the present invention may be prepared from blood plasma or serum of patients and carriers infected with HB virus by a conventional method, for instance, by treating the blood plasma with calcium chloride, salting out with ammonium sulfate, centrifuging, and adding ammonium sulfate to the resulting supernatant fluid, and thereby precipitating HBs antigen.

The partially purified HBs antigen thus prepared is applied onto a column filled with an anion exchanger which is previously equilibrated with an appropriate buffer solution having an ionic strength ($\mu$) of 0.02 to 0.1, preferably 0.04 to 0.06, and a pH level of 5.0 to 7.0, preferably 5.4 to 5.6, (e.g. acetate buffer, citrate buffer, phosphate buffer, succinate buffer, phthalate buffer, etc.). By this treatment, the HBs antigen and plasma protein comprising mainly $\gamma$-globulin pass through the column without being adsorbed thereon and other plasma proteins such as albumin, $\alpha$- and $\beta$-globulins, etc. are adsorbed thereon.

The HBs antigen-containing effluent passed through the above anion exchanger column, which contains still some impurities comprising predominantly $\gamma$-globulin, is then applied onto a column filled with a cation exchanger, which is also previously equilibrated with an appropriate buffer solution having an ionic strength ($\mu$) of 0.02 to 0.14, preferably 0.06 to 0.09, and a pH level of 4.5 to 6.0, preferably 5.0 to 5.3, (e.g. acetate buffer, citrate buffer, phosphate buffer, succinate buffer, and phthalate buffer, etc.). By this treatment, the HBs antigen passes through the column without being adsorbed thereon and the plasma proteins such as $\gamma$-globulin contaminated into the HBs antigen are almost completely removed. Moreover, the HBs antigen obtained by the present invention does almost not contain Dane particles of HB virus and has a high purity.

Thus, the present invention can provide a highly purified HBs antigen from blood plasma or serum by simple procedures which can be done in an industrial scale without and difficulty, and the HBs antigen obtained by the present invention is useful for preparing a source of safe and stable vaccine for preventing viral hepatitis type B.

The present invention is illustrated by the following examples but is not limited thereto.

EXAMPLE 1

Step 1: Blood plasma, which was positive in HBe antibody, was treated with calcium chloride and dextran sulfate. The supernatant fluid was separated and salted out with 1.2 M ammonium sulfate. After centrifugation, to the supernatant fluid was added 1.8 M ammonium sulfate to precipitate HBs antigen. By this salting out, about 80% by weight of the components of human blood plasma were removed, and the HBs antigen-containing solution was concentrated to about 1/10 by volume.

Step 2: DEAE-Sepharose CL-6B gel (made by Pharmacia & Co.) was sufficiently equilibrated with acetate buffer (ionic strength: 0.05, pH: 5.5) and then the DEAE Sepharose CL-6B gel thus treated was filled into a column. The HBs antigen-containing solution obtained in the above step 1 was sufficiently dialyzed against the same acetate buffer as above, and the resulting precipitate was removed by centrifugation, and the HBs antigen-containing solution thus obtained was applied onto the above column filled with DEAE-Sepharose CL-6B gel. The column was eluted with acetate buffer of which ionic strength was varied stepwise by adding sodium chloride.

Each fraction of the effluent and of the eluate with acetate buffer, was measured in terms of the content of HBs antigen and other proteins. The content of HBs antigen was estimated by immuno-electrosyneresis (abbreviation: IES) and shown by titer [cf. Bussard, A., B.B.A., Vol. 34, page 258 (1959)], and the content of proteins was measured by optical density at 280 nm ($OD_{280}$). The results are shown in the accompanying FIG. 1, wherein the HBs antigen is shown by a solid line and other proteins are shown by a dotted line. As is clear from FIG. 1, HBs antigen passed through the column of an anion exchanger and was contained in the effluent, and other proteins than HBs antigen and $\gamma$-globulin were adsorbed onto the column and eluted with eluting acetate buffer (ionic strength ($\mu$): 0.15, 0.3 and 0.6). The proteins contaminated in the effluent (ionic strength ($\mu$): 0.05) were mainly $\gamma$-globulin. Moreover, about 80% by weight of HBs antigen passed through the column, and the degree of purification of HBs antigen was about 14 times in comparison with the starting material.

Step 3: CM-Sepharose CL-6B gel (made by Pharmacia & Co.) was sufficiently equilibrated with acetate buffer (ionic strength: 0.08, pH: 5.1) and then was filled into a column. The effluent obtained in the above step 2 was sufficiently dialyzed against the same acetate buffer as above and then applied onto the above column filled with CM-Sepharose CL-6B gel. The column was eluted with acetate buffer of which ionic strength was varied stepwise by adding sodium chloride.

Figure 2:
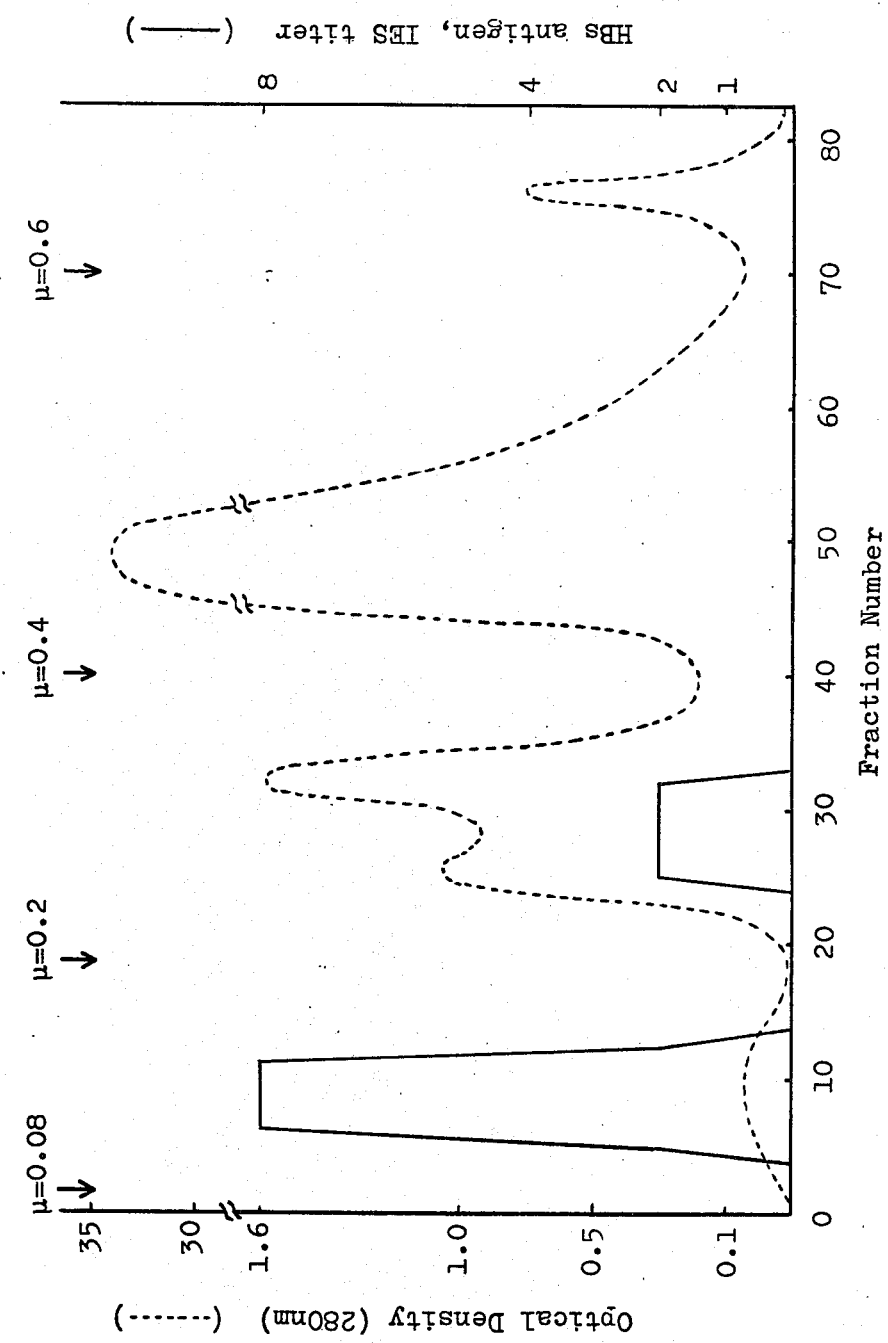

Each fraction of the effluent and of the eluate with acetate buffer was measured in terms of the content of HBs antigen and other proteins in the same manner as in the above step 2. The results are shown in FIG. 2, wherein the HBs antigen is shown by a solid line and other proteins are shown by a dotted line. As is clear from FIG. 2, HBs antigen again passed through the column of a cation exchanger and was contained in the effluent, and the remaining plasma proteins comprising mainly γ-globulin were adsorbed onto the column and eluted with eluting acetate buffer (ionic strength ($\mu$): 0.2, 0.4 and 0.6). That is, the effluent consisted essentially of HBs antigen and contained almost no other proteins. Moreover, about 24 to 48% by weight of HBs antigen was recovered in the effluent and the degree of purification was increased to 1500 times in comparison with the starting material.

In the following Table 1, there are shown the degree of purification and recovery of HBs antigen in each step of the above procedure.

Table 1

| Purification step | Volume (ml) | Concentration of protein* (% by weight) | Remaining protein (% by weight) | IES titer of HBs antigen | Specific activity (Protein concentration/IES titer) | Recovery of HBs antigen (% by weight) |
|---|---|---|---|---|---|---|
| Starting blood plasma | 500 | 7.5 | 100 | 1 : 4 | 1 | 100 |
| After salting out with ammonium sulfate | 60 | 9.2 | 15.0 | 1 : 32 | 6.53 | 96 |
| After chromatography with DEAE-Sepharose CL-6B | 100 | 2.1 | 5.60 | 1 : 16 | 14.3 | 80 |
| After chromatography with CM-Sepharose CL-6B | 120 | 0.005 | 0.016 | 1 : 8 | 1500 | 24–48 |

[Remark]:
*The protein concentration was estimated with absorbance at UV 280 nm.

When the HBs antigen-containing effluent finally obtained above was tested by reversed passive hemogglutination (abbreviation: r-PHA) [cf. Juji, T and Yokochi, T, Jap. J. Exp. Med., Vol. 39, Page 615 (1969)], the agglutination occurred till 1024 times dilution and this diluted mixture had such a small protein concentration as 6 μg/ml (measured by Kjeldahl method). Besides, even when the effluent was concentrated to 1/100 by volume, no serum component was detected by an immuno-diffusion method and immuno-electrophoresis.

Moreover, in order to prove the purity of HBs antigen-containing effluent obtained by the above ion exchange chromatography the following test was done. Each fraction at purification steps was analyzed by immunoelectrophoretically using antibodies to normal human plasma components. The results of the test revealed that the effluent of an anion exchanger (DEAE-Sepharose CL-6B) contained a little of plasma components comprising predominantly γ-globulin as a contaminant, but the final effluent of an cation exchanger (CM-Sepharose CL-6B) contained nothing impurity other than HBs antigen. By contrary, the eluates of both ion exchangers showed that they contained all of the impurities originated in plasma components. Besides, to confirm whether the finally purified HBs antigen contained any impurity such as serum proteins, it was injected to rabbits, and there was observed in those animals nothing antibody except that to HBs.

Furthermore, the finally purified product (the degree of purification: 1500 times, recovery: 24–48% by weight) was analysed by a density gradient ultracentrifugation using sucrose and cesium chloride. As a result, the HBs antigen had a peak at the concentration of sucrose of 37% by weight and had also a peak at the $\rho = 1.207$ g/cm$^3$ of cesium chloride, and further showed a single sharp peak by r-PHA method, which means that the HBs antigen obtained is pure and homogeneous. Besides, it was also confirmed by an electron microscopic analysis that the final preparation of HBs antigen consisted of dispersed spherical particles alone having a size of 22 nm.

EXAMPLE 2

In the same manner as described in Example 1 except that a citrate buffer (ionic strength ($\mu$): 0.05, pH: 5.5) was used instead of the acetate buffer, a blood plasma, which was positive of HBe antigen, was treated, wherein the behavior of Dane particle was observed by surveying the HBc antigen. The survey of HBc antigen was carried out at a fixed titer of HBs antigen (16,000 times by r-PHA method). The results are shown in Table 2.

Table 2

| | | r-PHA titer | |
|---|---|---|---|
| Purification step | Volume (ml) | HBs antigen | HBc antigen |
| Starting serum which is positive in HBe antigen | 450 | 16,000 | 16 |
| Precipitate salted out with 1.2 M ammonium sulfate | 160 | 16,000 | 32 |
| Precipitate salted out with 1.8 M ammonium sulfate | 440 | 16,000 | 8 |
| DEAE-Sepharose CL-6B column chromatography: | | | |
| Effluent | 100 | 16,000 | <2 |
| Eluate with citrate buffer ($\mu=0.15$) | 140 | 16,000 | <2 |
| Eluate with citrate buffer ($\mu=0.3$) | 40 | 16,000 | 32 |
| CM-Sepharose CL-6B column chromatography: | | | |
| Effluent | 30 | 16,000 | <2 |
| Eluate with citrate buffer ($\mu=0.2$) | 5 | 2,000 | <2 |

EXAMPLE 3

A blood serum, which was positive of HBe antibody, was pretreated in the same manner as described in Example 1, step 1.

DEAE-cellulose (made by Serva & Co.) was activated and sufficiently equilibrated with citrate buffer (ionic strength ($\mu$): 0.04, pH: 5.5), and then was filled into a column. The above pretreated HBs antigen-containing solution was sufficiently dialyzed against the same buffer and then was applied onto the above column filled with DEAE-cellulose.

CM-Sephadex C-25 (made by Pharmacia & Co.) was sufficiently equilibrated with citrate buffer (ionic strength ($\mu$): 0.055, pH: 5.3) and then was filled into a column. The effluent passed through the first column of DEAE-cellulose was sufficiently dialyzed against the second citrate buffer as above and then applied onto the second column of CM-Sephadex C-25. The results are shown in Table 3.

Table 3

| Purification step | Volume (ml) | Concentration of protein (% by weight) | IES titer of HBs antigen | Specific activity (protein concentration/ IES titer) | Recovery of HBs antigen (% by weight) |
|---|---|---|---|---|---|
| Starting material | 100 | 7.4 | 1 : 32 | 1 | 100 |
| Material after pretreatment | 20 | 5.0 | 1 : 128 | 6.0 | 80–100 |
| Effluent obtained after chromatography with DEAE-cellulose | 100 | 0.4 | 1 : 16 | 9.3 | 50 |
| Effluent obtained after chromatography with CM-Sephadex C-25 | 200 | 0.002 | 1 : 4 | 463 | 25 |

As is clear from Table 3, 50% by weight of HBs antigen was recovered into the effluent passed through the DEAE-cellulose column and the degree of purification was increased to 9.3 times of that of the starting material. This effluent was contaminated with serum proteins which comprised mainly $\gamma$-globulin. Besides, 25% by weight of the HBs antigen was recovered into the effluent passed through the CM-Sephadex C-25 column, and the degree of purification was increased to 463 times to that of the starting material. In this effluent, no serum protein was observed by immuno-electrophoresis.

What is claimed is:

1. A method for purification of HBs antigen, which comprises passing an HBs antigen-containing solution prepared from blood plasma or serum through an anion exchanger and then passing the resulting effluent through a cation exchanger.

2. A method for purification of HBs antigen according to claim 1, wherein the anion exchanger is previously equilibrated with a buffer solution having an ionic strength of 0.02 to 0.1 and a pH level of 5.0 to 7.0, and the cation exchanger is previously equilibrated with a buffer solution having an ionic strength of 0.02 to 0.14 and a pH level of 4.5 to 6.0.

3. A method for purification of HBs antigen according to claim 2, wherein the buffer solution for treating the anion exchanger has an ionic strength of 0.4 to 0.06 and a pH level of 5.4 to 5.6, and the buffer solution for treating the cation exchanger has an ionic strength of 0.06 to 0.09 and a pH level of 5.0 and 5.3.

4. A method for purification of HBs antigen according to claim 2 or 3, wherein the HBs antigen-containing solution is dialyzed against the buffer solution to enable the anion exchanging optimal before passing through the anion exchanger and the effluent is dialyzed against the buffer solution to enable the cation exchanging optimal before passing through the cation exchanger.

* * * * *